US010159434B1

(12) United States Patent
Alla et al.

(10) Patent No.: US 10,159,434 B1
(45) Date of Patent: Dec. 25, 2018

(54) SYSTEMS AND METHODS FOR OPTODE IMAGING

(71) Applicant: Verily Life Sciences LLC, Mountain View, CA (US)

(72) Inventors: Suresh Alla, San Jose, CA (US); John D Perreault, Mountain View, CA (US); Victor Marcel Acosta, San Francisco, CA (US); Seung Ah Lee, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 448 days.

(21) Appl. No.: 14/954,331

(22) Filed: Nov. 30, 2015

(51) Int. Cl.
*A61B 5/1455* (2006.01)
*A61B 5/1459* (2006.01)
(Continued)

(52) U.S. Cl.
CPC ........ *A61B 5/1459* (2013.01); *A61B 5/14546* (2013.01); *A61B 5/7203* (2013.01); *A61B 5/7278* (2013.01); *A61B 5/0059* (2013.01); *A61B 5/0071* (2013.01); *A61B 5/1451* (2013.01); *A61B 5/14503* (2013.01);
(Continued)

(58) Field of Classification Search
CPC ..... A61B 5/0017; A61B 5/0059; A61B 5/076; A61B 5/0086; A61B 5/1411; A61B 5/14532; A61B 5/14533; A61B 5/14546; A61B 5/1455; A61B 5/14552; A61B 5/14553; A61B 5/14556; A61B 5/14558; A61B 5/1459; A61B 5/6867;
(Continued)

(56) References Cited

U.S. PATENT DOCUMENTS 3,971,065 A    7/1976  Bayer
5,431,170 A *  7/1995  Mathews ............. A61B 5/0002
                                                600/323
(Continued)

OTHER PUBLICATIONS

Zhao et al., Automated Autofluorescence Background Subtraction Algorithm for Biomedical Raman Spectroscopy, Applied Spectroscopy, vol. 61, No. 11, Nov. 2007, pp. 1225-1232.*
(Continued)

*Primary Examiner* — Eric Winakur
*Assistant Examiner* — Darin Janoschka
(74) *Attorney, Agent, or Firm* — McDonnell Boehnen Hulbert & Berghoff LLP

(57) ABSTRACT

Methods and systems disclosed herein may be operable to detect a presence or absence of an analyte in human tissue. An example method includes operating one or more light sources to illuminate a plurality of optodes with excitation light. Each optode is embedded in tissue at a respective location. The excitation light causes the optodes to emit emission light and the optodes are sensitive to at least one analyte such that the emission light emitted by the optodes is indicative of a presence or absence of at least one analyte in the tissue. An optical filter arrangement includes for each optode in the plurality of optodes a corresponding set of one or more optical filters. The method includes obtaining detector information from a detector arrangement optically coupled to the optical filter arrangement, and detecting the at least one analyte based on the detector information.

21 Claims, 12 Drawing Sheets

(51) Int. Cl.
*A61B 5/145* (2006.01)
*A61B 5/00* (2006.01)
*G01N 21/64* (2006.01)

(52) U.S. Cl.
CPC ............ *A61B 2562/0233* (2013.01); *A61B 2562/0238* (2013.01); *A61B 2562/0285* (2013.01); *A61M 2205/3303* (2013.01); *G01N 21/6428* (2013.01); *Y10S 977/957* (2013.01)

(58) Field of Classification Search
CPC .. A61B 5/0071; A61B 2562/0285; G01J 3/10; G01N 21/64; G01N 21/78
USPC ................................................ 600/300–399
See application file for complete search history.

(56) References Cited

U.S. PATENT DOCUMENTS

| | | | | |
|---|---|---|---|---|
| 5,628,310 | A * | 5/1997 | Rao | A61B 5/0017 600/317 |
| 5,813,403 | A * | 9/1998 | Soller | A61B 5/0075 600/310 |
| 6,236,870 | B1 * | 5/2001 | Madarasz | A61B 5/14558 356/364 |
| 6,591,121 | B1 * | 7/2003 | Madarasz | A61B 5/14558 356/364 |
| 6,694,158 | B2 * | 2/2004 | Polak | A61B 5/14532 600/310 |
| 7,259,853 | B2 * | 8/2007 | Hubble, III | G01J 3/10 356/319 |
| 7,863,038 | B2 * | 1/2011 | Motamedi | A61B 5/14532 427/2.11 |
| 8,442,606 | B2 * | 5/2013 | Furman | A61B 5/0031 600/323 |
| 8,527,035 | B2 | 9/2013 | Diamond | |
| 8,914,090 | B2 * | 12/2014 | Jain | A61B 5/0017 600/309 |
| 9,974,471 | B1 * | 5/2018 | Kam | A61B 5/14514 |
| 2005/0054908 | A1 * | 3/2005 | Blank | A61B 5/0075 600/316 |
| 2008/0068735 | A1 | 3/2008 | Goldsmith | |
| 2014/0162372 | A1 | 6/2014 | Park et al. | |

OTHER PUBLICATIONS

Alla et al., Nanoporous Thin Film Platform for Biophotonic Sensors, SPIE BiOS Conference, Feb. 2009, pp. 1-9.*

* cited by examiner

Top View

Cross-Sectional View

Cross-Sectional View

SYSTEMS AND METHODS FOR OPTODE IMAGING

BACKGROUND

Medical diagnostic information about living tissue may be obtained by a variety of optical means. For example, an optical sensor, e.g. an optode, may be configured to provide a characteristic optical response when in proximity to an analyte in the tissue. The optical response may be read out by a detector.

SUMMARY

In an aspect, a system is provided. The system includes one or more light sources. The one or more light sources are operable to illuminate a plurality of optodes with excitation light. Each optode is embedded in tissue at a respective location. The excitation light causes the optodes to emit emission light. The optodes are sensitive to at least one analyte such that the emission light emitted by the optodes is indicative of a presence or absence of at least one analyte in the tissue. The system also includes an optical filter arrangement. The optical filter arrangement includes for each optode in the plurality of optodes a corresponding set of one or more optical filters. The system further includes a detector arrangement optically coupled to the optical filter arrangement. The detector arrangement includes for each optode in the plurality of optodes a corresponding set of one or more detectors operable to detect light received from the optode's respective location via the optode's corresponding set of one or more optical filters. The system yet further includes a controller having at least one processor. The controller is programmed to carry out operations. The operations include operating the one or more light sources to illuminate the plurality of optodes with excitation light. The system also includes operating the detector arrangement to obtain detector information. The detector information includes for each optode a respective optode signal indicative of light that has been emitted from the optode's respective location in response to the illumination from the one or more light sources, filtered through the optode's corresponding set of one or more optical filters, and detected by the optode's corresponding set of one or more detectors. The system yet further includes detecting the at least one analyte based on the detector information.

In an aspect, a method is provided. The method includes operating one or more light sources to illuminate a plurality of optodes with excitation light. Each optode is embedded in tissue at a respective location. The excitation light causes the optodes to emit emission light, and the optodes are sensitive to at least one analyte such that the emission light emitted by the optodes is indicative of a presence or absence of at least one analyte in the tissue. An optical filter arrangement includes for each optode in the plurality of optodes a corresponding set of one or more optical filters. The method also includes operating a detector arrangement to obtain detector information. The detector arrangement is optically coupled to the optical filter arrangement and the detector arrangement includes for each optode in the plurality of optodes a corresponding set of one or more detectors operable to detect light received from the optode's respective location via the optode's corresponding set of one or more optical filters. The detector information includes for each optode a respective optode signal indicative of light that has been emitted from the optode's respective location in response to the illumination from the one or more light sources, filtered through the optode's corresponding set of one or more optical filters, and detected by the optode's corresponding set of one or more detectors. The method yet further includes detecting the at least one analyte based on the detector information.

Other aspects, embodiments, and implementations will become apparent to those of ordinary skill in the art by reading the following detailed description, with reference where appropriate to the accompanying drawings.

DETAILED DESCRIPTION

I. Overview

Figure 1:
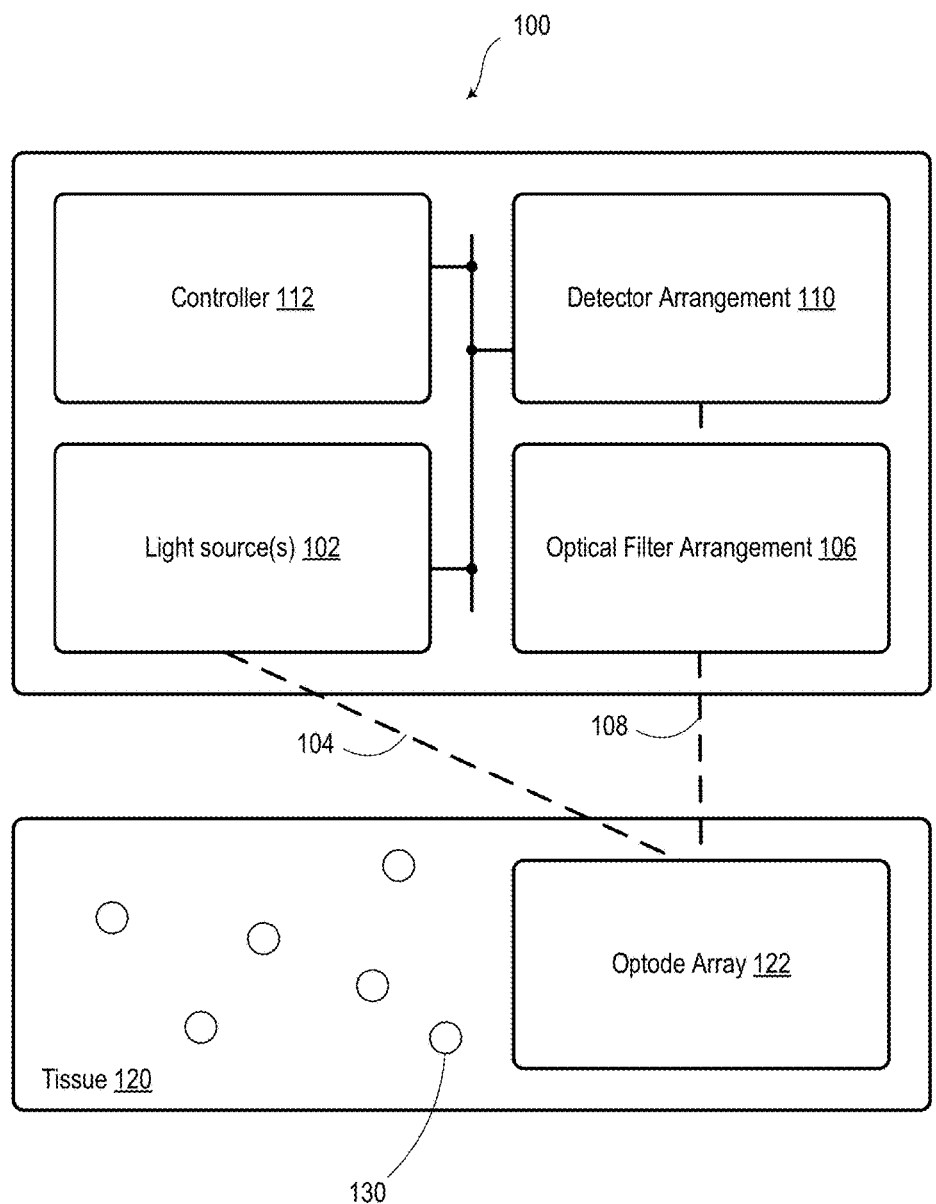
FIG. 1 illustrates a system, according to an example embodiment.

The systems and methods described herein may provide diagnostic information about tissue via optical means. For example, the systems may include an optode or another type of chemical sensor configured to change its optical properties while in proximity to a particular analyte.

Optodes may provide a characteristic optical response while in proximity to an analyte. In general, each optode may include a chemical configured to provide an optical response when in proximity to the analyte. For example, the chemical may have a given fluorescence spectrum that is at least partially quenched or attenuated when the analyte is nearby. Furthermore, the optodes may be incorporated into various physical structures, such as nanoparticles and/or polymer matrices. As such, the optodes may be interrogated as optical sensor devices that may measure a presence, concentration, and/or location of the analyte.

In such an example, the optode may be illuminated by an excitation light source. In response to receiving light at the excitation wavelength, certain chemicals such as fluorophores in the optode may emit emission light. When in proximity of the specific analyte, the emission behavior may be increased, decreased, or otherwise affected.

Optical filters may exhibit selective transmission of light based on polarization and/or wavelength. That is, optical filters may transmit light at some polarizations and/or wavelengths, but not at others. Additionally or alternatively, optical filters may provide varying degrees of attenuation based on the polarization and/or wavelength of incoming light. Furthermore, such optical filters may be placed in an optical path between a light source and detector so as to attenuate, modify, or otherwise filter light incident on the detector.

In an example embodiment, an optical filter plate may include a plurality of optical filters arranged to correspond spatially with the optode arrangement. The optical filter plate may be optically coupled to a detector array, such as an array of charge-coupled devices (CCD) and/or a focal plane array (FPA). In such a scenario, the optical filter plate may filter the light emitted from the optodes so as to provide a recognizable optical pattern to the detector array. Accordingly, the systems described herein may be used to detect a concentration, presence, or lack thereof of the specific analyte.

The systems and methods described herein may enable a variety of applications. In some example embodiments, the systems and methods herein may be used for intra-operative tumor imaging. For instance, an arrangement of optodes may be injected or otherwise applied to the skin tissue near a known cancer tumor site. The optodes may be configured to provide a characteristic optical response when in proximity to cancer cells or a specific marker that may bind to such cells. As such, the imaging of such optodes via the optical filter arrangement may provide information indicative of the surgical margins of the cancer tumor. Furthermore, such imaging may proceed during and after surgery to confirm complete resection of the tumor.

In an example embodiment, the systems described herein may be incorporated into a surgical robot. For example, the surgical robot may obtain information about tissue to be removed and tissue to be preserved via the present system. In the scenario above involving a cancer tumor, the surgical robot may periodically or continuously image the surgical site during surgery to identify cancerous tissue for removal (e.g. via laser cutting) and/or identify non-cancerous tissue for preservation.

The systems and methods described herein may be incorporated into a wearable device. For example, a wrist-mountable device may incorporate the light source, optical filter arrangement, and detector array as described herein. Additionally or alternatively, the wearable device may be worn elsewhere on the body. For example, the wearable device may be mountable or positionable on a back, a chest, an arm, a hand, a finger, a head, or other parts of the body.

In some embodiments, the present application may enable an optical biopsy. That is, by applying an array of optodes near or in a suspect skin growth or skin spot, information about the skin growth or spot may be obtained. As an example, the optodes may be configured to provide information about the presence of malignant melanoma cells. As such, the skin growth or spot may be interrogated without physical removal of tissue. It is understood that similar biopsy or medical diagnoses are possible via optical means with the present systems and methods.

Point of care applications are also possible. For example, an array of optodes may be applied to infected skin tissue, e.g. cellulitis. The optodes in such a scenario may be configured to provide a characteristic optical response when in proximity to a bacteria or a biomarker bound to such bacteria. Imaging the optodes via the optical filter arrangement may help visualize the progression of the infection and identify locations where medication (e.g. topical ointment, injection) may be delivered.

II. Example Systems

FIG. 1 illustrates a system 100, according to an example embodiment. System 100 includes at least one light source 102, an optical filter arrangement 106, a detector arrangement 110, and a controller 112. At least some of the elements of system 100 may be arranged in a wearable device. For example, system 100 may take the form of a smartwatch, necklace, armband, headband, chest strap, or another type of wearable device. In some embodiments, system 100 may be incorporated into clothing.

At least some of the elements of system 100 are configured to interact with and/or interrogate an optode array 122 embedded in tissue 120, as described herein.

The at least one light source 102 may include a laser, such as a single-mode laser configured to provide excitation light 104 in the visible or near-infrared wavelengths. However, multi-mode lasers, wavelength-adjustable lasers, diode lasers, gas lasers, and broadband light sources such as light-emitting diodes (LEDs) are also contemplated. Furthermore, other wavelengths and wavelength ranges are considered herein. Specifically, the at least one light source 102 may be configured to provide excitation light 104 at one or more excitation wavelengths of at least one optode in the optode array 122.

The at least one light source 102 may be configured or arranged in various positions so as to provide excitation light 104 to the optode array 122. In an example embodiment, the at least one light source 102 may include a plurality of micro-LED arranged around the optical filter arrangement 106. Other configurations are possible. For example, a plurality of micro-LEDs and/or lasers may be interspersed or interleaved around the filters of the optical filter arrangement 106. For example, filters and light sources may be arranged in a checkerboard pattern. In another example embodiment, the light sources 102 may be disposed in an interleaved arrangement with respect to the detectors in the detector arrangement 110. In a further embodiment, the light source 102 may include a scanning light source, such as a scanning laser. In such a scenario, light from the scanning laser may be directed toward a scanning galvanometer and towards a portion of the skin tissue 120.

Additionally or alternatively, the system 100 may include a spatial light modulator. In such a scenario, the operations may include selecting a target optode from the plurality of optodes. The operations may further include controlling the spatial light modulator to direct the excitation light toward at the target optode in the plurality of optodes from the one or more light sources 102.

While FIG. 1 illustrates the at least one light source 102 as illuminating the optode array 122 from a location proximate to the optical filter arrangement 106, other arrangements are possible. For example, the light source 102 may illuminate the optode array 122 from another location. In an example embodiment, the light source 102 may illuminate the optode array 122 from an opposite side of the tissue 120. That is, the system 100 may allow transillumination of the excitation light through an earlobe, a nostril, or another soft tissue region of the body. Other arrangements of the light source(s) 102, the optode array 122 and the optical filter arrangement 106 are contemplated herein.

In some embodiments, the system 100 may include a diffuser that may be configured to diffuse the light of the at least one light source 102. For example, the one or more light sources 102 may be optically-coupled to the diffuser, which may be disposed around the detector arrangement 110. That is, the diffuser may be disposed around an outer periphery of an optical path between the detector arrangement 110 and the optode filter arrangement 106. Additionally or alternatively, the diffuser may be located elsewhere.

In an example embodiment, the optode array 122 may include one or more optodes. In turn, each optode may include a fluorophore or a dye configured to change its optical properties when near an analyte 130. For example, each optode of the optode array 122 may be configured to change its respective optical properties in the presence of a different respective analyte. As such, each optode of the optode array 122 may be configured to sense a different analyte. Furthermore, various combinations of optodes may be combined, arranged, or ordered in the optode array 122 so as to improve the accuracy and/or repeatability of analyte detection.

The words "near", "proximate", or "nearby" as used herein with respect to an analyte may indicate a distance between the analyte and a given optode of the optode array 122. In some embodiments, "near", "proximate", or "nearby" may relate to a distance of less than 50 microns. However, other distances are possible. For example, optodes may be sensitive to analytes present within distances up to 1 millimeter.

Furthermore, the optical response of a respective optode may be based on the concentration of the analyte. Namely, the optical response (e.g. fluorophore quenching) may scale with analyte concentration. The systems and methods described herein may be operable to detect very low analyte concentration levels. For example, such systems may be operable to detect 10 ng/mL or less of analyte in solution (e.g. blood and/or interstitial fluid).

The analyte 130 may represent one or more target analytes of interest that may be detected and measured in the human body. For example, the analyte 130 may include glucose, a biomarker, a particular cell type (e.g., a cancer cell), or another type of target analyte. As described above, the systems and methods described herein may be operable to detect several analytes in a single detection cycle. The analyte 130 could be present in interstitial fluid or other bodily fluid.

The optical filter arrangement 106 may include one or more optical elements. The one or more optical elements may include a bandpass filter, a longpass filter, a shortpass filter, a dichroic filter, a polarization filter, an interference filter, an absorptive filter, a dielectric stack, a bandstop filter, a lens, a diffuser, or another type of optical element. The optical filter arrangement 106 may be arranged substantially along a plane so that different spatial regions along the plane may have different light transmission characteristics depending upon where light impinges along the optical filter arrangement 106.

The detector arrangement 110 may be optically coupled to the optical filter arrangement 106. In an example embodiment, the detector arrangement 110 may include a focal plane array or an image sensor configured to sense light transmitted through the optical filter arrangement 106. In other words, the detectors in detector arrangement 110 may be operable to detect light transmitted through the optical filter arrangement 106 from the optodes of optode array 122.

The detector arrangement 110 may include one or more charge coupled devices (CCDs) or complementary metal oxide semiconductor (CMOS) detectors.

Controller 112 may be coupled to light source 102 and detector 110. The controller 112 may include a memory in which to store instructions. The controller 112 may also include a processor configured to carry out various operations based on the instructions. Namely, the operations may include the controller 112 operating the one or more light sources 102 to illuminate the optode array 122 with excitation light.

The operations may also include operating the detector arrangement 110 to obtain detector information. Namely, the detector information may include for each optode a respective optode signal indicative of light that has been emitted from the optode's respective location in response to the illumination from the one or more light sources 102, filtered through the optode's corresponding set of one or more optical filters in the optical filter arrangement 106, and detected by the optode's corresponding set of one or more detectors.

Furthermore, the operations include detecting the at least one analyte based on the detector information. For example, detecting the at least one analyte may be based on a characteristic optical signal being received by one or more detectors of the detector arrangement 110. The characteristic optical signal may include signals from a particular combination of optodes, an optical signal indicative of quenching, enhancement, or another modification of a given waveband or wavelength of an optode optical response. Other characteristic optical signals are possible.

System 100 may be configured to carry out operations related to filtering at least a portion of a background signal based on information provided from the detector information. In an example embodiment, the background signal may include a tissue autofluorescence signal. That is, tissues naturally emit light when illuminated by certain wavelengths of light. In such an embodiment, the controller 112 may be configured to adjust the detector information based on the background signal. Additionally or alternatively, the controller 112 may adjust one or more of the optode signals based on a corresponding portion of the background signal.

In yet another embodiment, the plurality of optode signals may each include an autofluorescence portion associated with tissue autofluorescence and an emission portion associated with emission light from the respective optodes. As such, the controller may be configured to adjust the emission light with respect to the corresponding autofluorescence portions.

Other ways of reducing the effect of tissue autofluorescence are contemplated herein.

FIGS. 2A-2D illustrate a scenario 200, according to an example embodiment. The elements of scenario 200 may be similar or identical to corresponding elements illustrated and described in reference to FIG. 1.

Figure 2A:
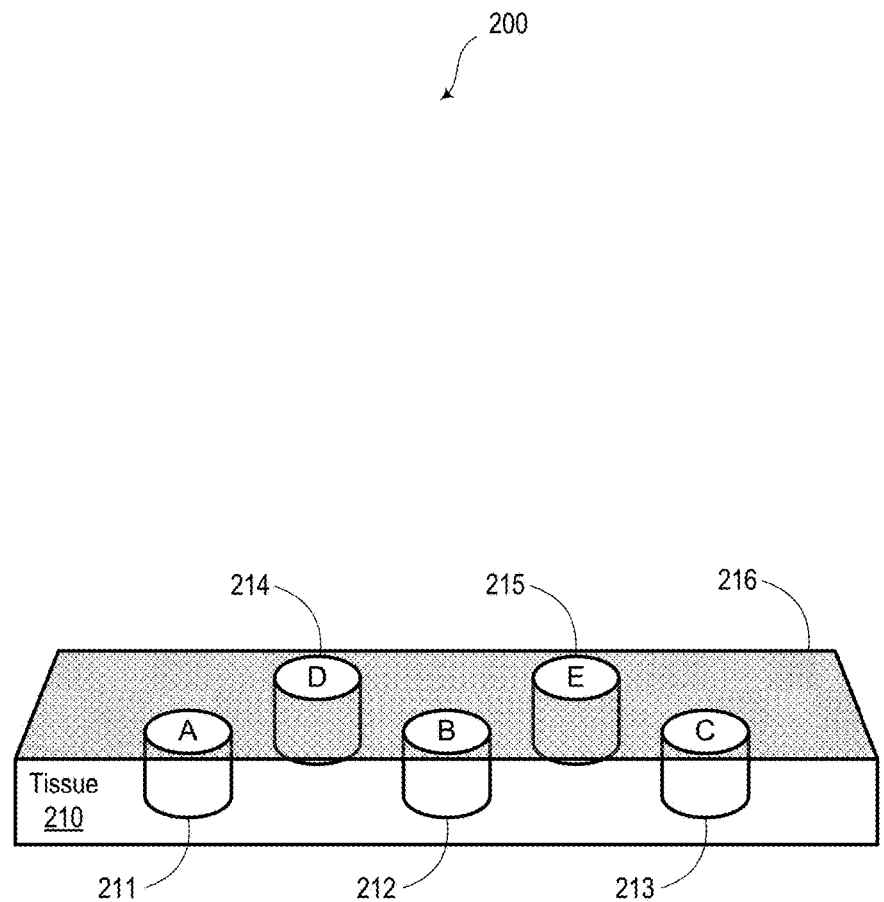
FIG. 2A illustrates a scenario, according to an example embodiment.

FIG. 2A illustrates embedding a plurality of optodes 211-215 into tissue 210 via a skin surface 216. That is, the plurality of optodes 211-215 may be injected or otherwise inserted into the tissue 210. The plurality of optodes 211-215 may be arranged in a particular two-dimensional or three-dimensional arrangement or pattern. Specifically, the arrangement of optodes may be asymmetric so as to avoid alignment ambiguity. As illustrated, FIG. 2A shows optodes 211-215 as disposed in two rows, with three and two columns in the respective rows. In such a configuration, the arrangement of optodes is less likely to be misread based on lateral or rotational misalignment between the optodes 211-215 and the readout device. The optodes 211-215 may be delivered to a depth of approximately 1 millimeter below the skin surface 216 (e.g., implanted in the dermis), however delivery to other skin depths is contemplated.

In an example embodiment, the plurality of optodes 211-215 may be configured to provide a change in an optical response based on a proximity to different analytes A through E. For example, optode 211 may be sensitive to analyte A, optode 212 may be sensitive to analyte B, and so on. In other embodiments, each optode may be sensitive to multiple analytes, or each of the optodes may be sensitive to the same analyte (e.g., analyte A).

In some example embodiments, a registration fiducial may be applied to the skin surface 216 or implanted into the skin. The registration fiducial may include a visible structure or mark, in the shape of a cross, a box, or another recognizable symbol. In such a scenario, the registration fiducial may be used by a robot or user to properly align the filter plate and detector array, as described below. In other embodiments, the registration fiducial may be invisible to the unaided eye. For example, the registration fiducial may include a characteristic arrangement of optodes configured to emit light at a characteristic wavelength or within a characteristic waveband.

Figure 2B:
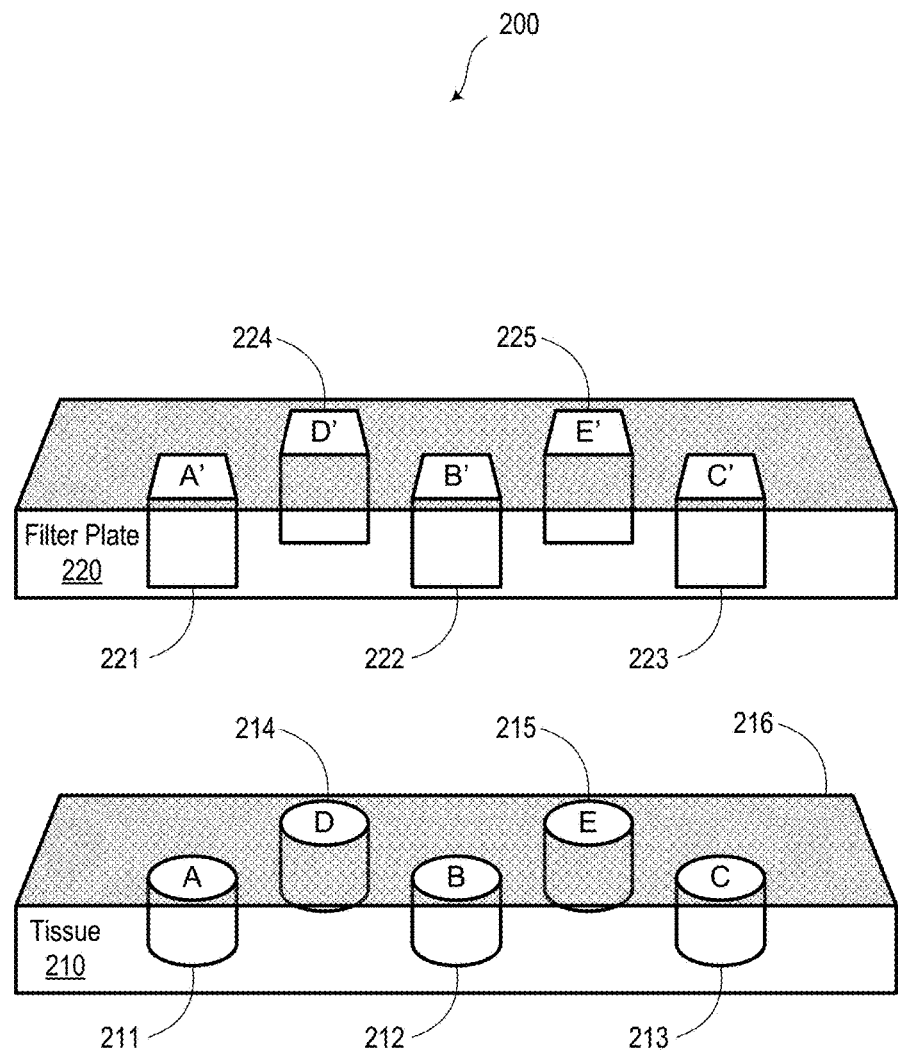
FIG. 2B illustrates a scenario, according to an example embodiment.

FIG. 2B illustrates a filter plate 220 that may include a plurality of optical filters 221-225. The plurality of optical filters 221-225 may be arranged along a surface of the filter plate 220 so as to spatially correspond to the plurality of optodes 211-215. For example, optical filter 221 may arranged so as to correspond with optode 211, optical filter 222 may be arranged so as to correspond with optode 212, and so on.

In an example embodiment, each optical filter may have a different optical transfer function (OTF). That is, as a function of the wavelength of light, optical filter 221 may transmit light differently than optical filter 222. For example, optical filter 221 may have an OTF configured to efficiently transmit a characteristic optical signal from optode 211 indicating a presence of analyte A. As a non-limiting example, optical filter 221 may include a bandpass filter. Specifically, the bandpass filter (A') may be configured to transmit at least a characteristic portion of light emitted from optode 211 in the presence of analyte A. Optical filter 222 may include a bandpass filter (B') that may be configured to transmit at least a characteristic portion of light emitted from optode 212 in the presence of analyte B. Furthermore, optical filter 223 may include a bandpass filter (C') that may be configured to transmit at least a characteristic portion of light emitted from optode 213 in the presence of analyte C. Also, optical filter 224 may include a bandpass filter (D') that may be configured to transmit at least a characteristic portion of light emitted from optode 214 in the presence of analyte D. Similarly, optical filter 225 may include a bandpass filter (E') that may be configured to transmit at least a characteristic portion of light emitted from optode 215 in the presence of analyte E. In an example embodiment, the characteristic portion of light may correspond with a characteristic waveband or plurality of wavebands.

In an example embodiment, the characteristic waveband may include a characteristic long wavelength cutoff and a characteristic short wavelength cutoff. In such a scenario, the one or more optical filters may include a shortpass filter having a cutoff wavelength less than the characteristic short wavelength cutoff. Furthermore, the one or more optical filters may include a longpass filter with a cutoff wavelength greater than the characteristic long wavelength cutoff.

Additionally or alternatively, optical filter 221 may include a bandstop filter and/or a notch filter. In another embodiment, the optical filters may include a prism, a polarization filter, or another type of optical element configured to modify one or more properties of light. It is understood that other optical filters and optical elements or combinations of such elements are possible so as to minimize the optical transmission of background signals (e.g. tissue autofluorescence) and maximize optical transmission of characteristic emission light from the optodes.

Although FIG. 2B illustrates a "one-to-one" relationship between the plurality of optodes 211-215 and the optical filters 221-225, other relationships are possible. For example, more than one optical filter may correspond spatially to each optode. Additionally or alternatively, more than one optode may correspond to each optical filter. Furthermore, while optical filters 221-225 are illustrated as discrete filter elements, it is understood that one or more slowly varying optical filter elements may make up the optical filter. That is, the filter plate 220 may include one slowly varying optical filter (e.g. a gradient filter).

In addition to the elements described above, FIG. 2C illustrates a detector array 230. The detector array 230 includes detector elements 231-235. The detector elements 231-235 may include detector pixels. In an example embodiment, the detector elements 231-235 include CCD or CMOS image sensor pixels. Detector elements 231-235 may include other types of devices configured to sense light, such as avalanche photodiodes, photoconductor, and other photosensitive devices.

Figure 2C:
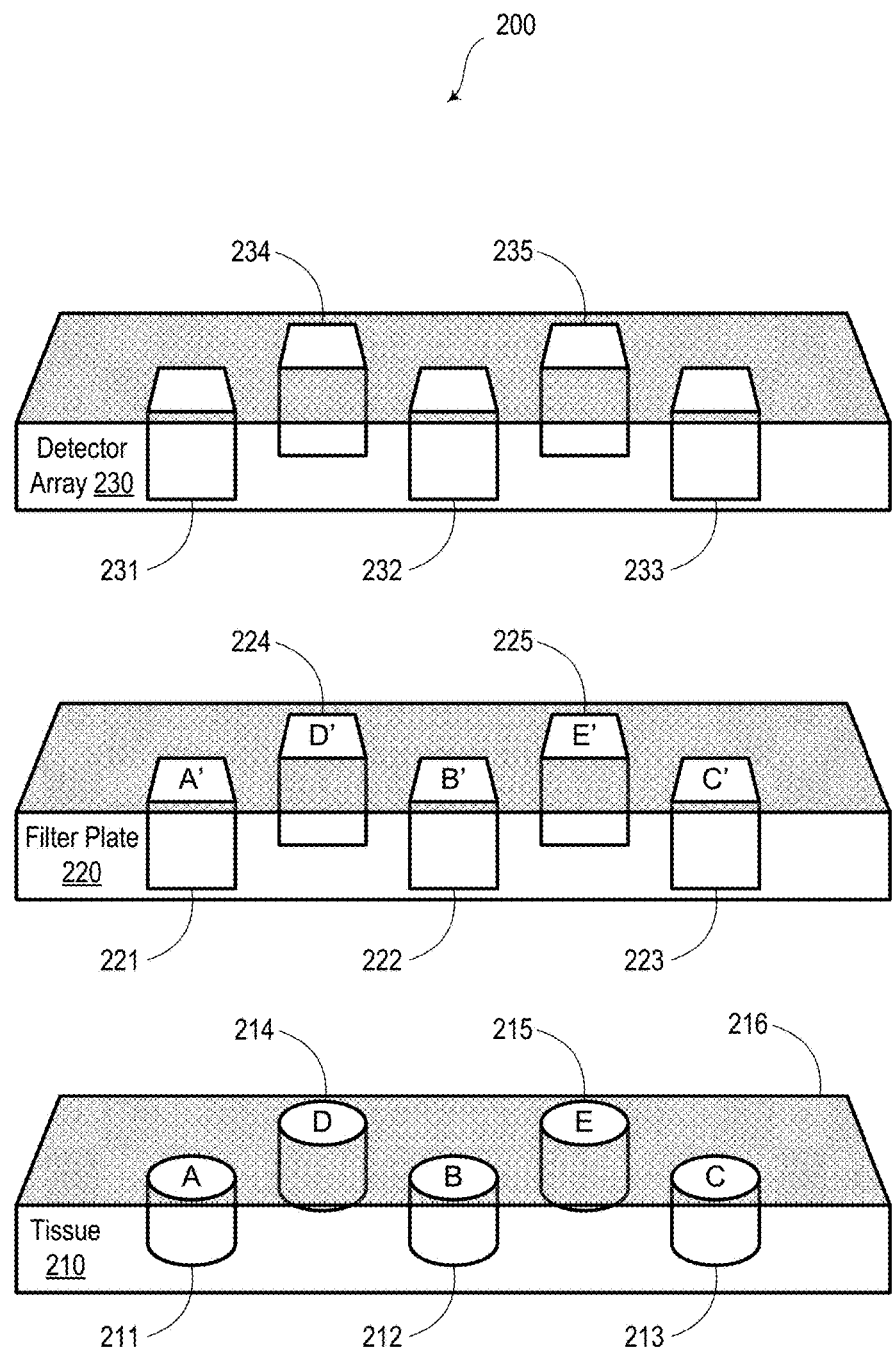
FIG. 2C illustrates a scenario, according to an example embodiment.

As illustrated in FIG. 2C, the detector array 230 and the detector elements 231-235 may correspond spatially to the optical filters 221-225 and/or the optodes 211-215. That is, the filter plate 220 may be fixed with respect to the detector array 230 such that the optical filters 221-225 provide transmitted light to one or more detector elements 231-235. Furthermore, the filter plate 220 and detector array 230 may be aligned or registered to the optode array in tissue 210. As described above, the registration may be performed via the registration fiducial.

In an example embodiment, emission light from the optode 211 may be filtered by optical filter 221 and sensed by detector element 231. Likewise, emission light from optode 212 may be filtered by optical filter 222 and sensed by detector element 232, and so on.

While FIG. 2C illustrates a "one-to-one" correspondence between the detector elements 231-235 and the optical filters 221-225, other relationships are possible. For example, a plurality of detector elements may correspond to a particular optical filter.

Figure 2D:
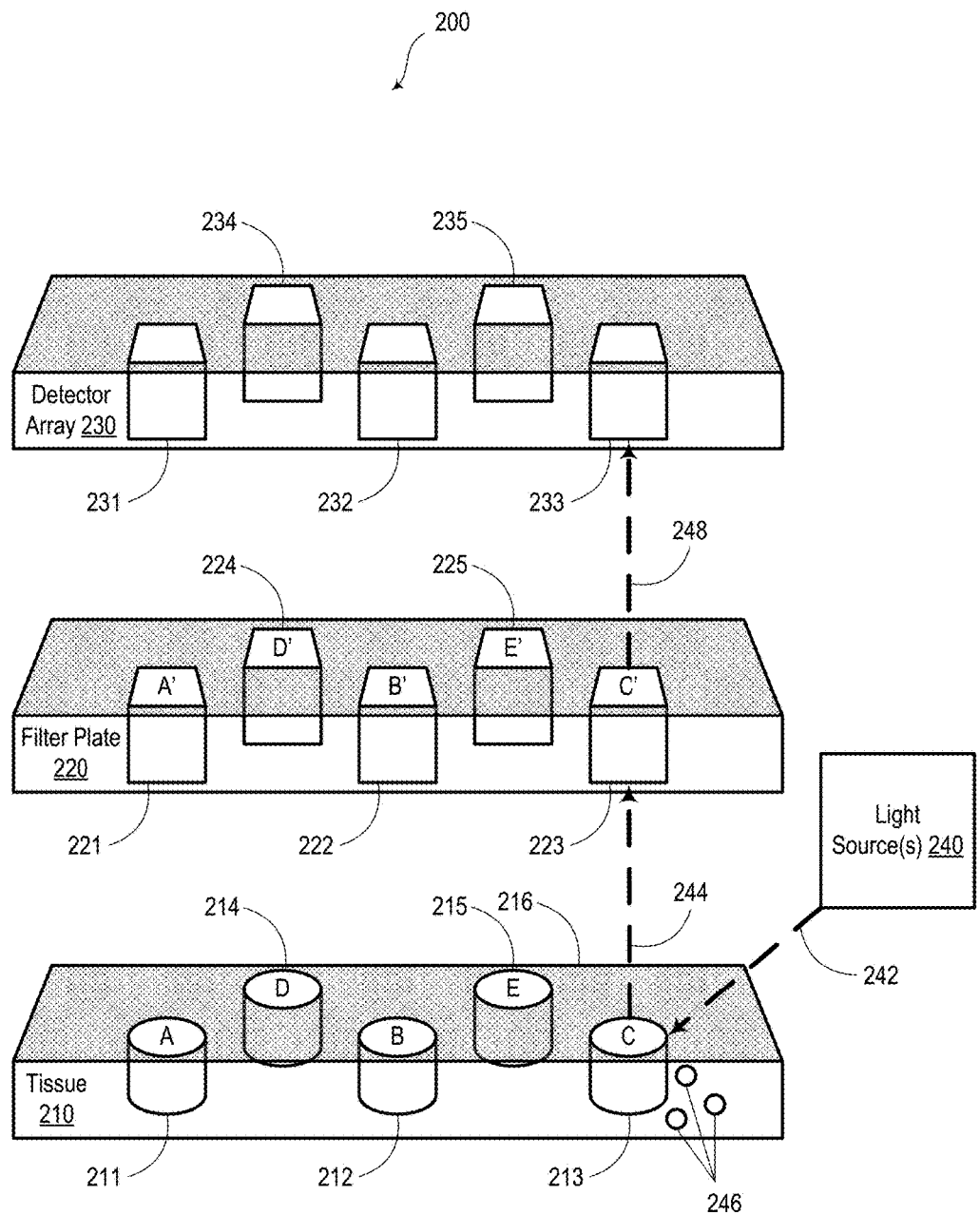
FIG. 2D illustrates a scenario, according to an example embodiment.

FIG. 2D illustrates a light source 240. As described herein, the light source 240 may include one or more lasers, LEDs, or other light-emitting devices. In an example embodiment, the light source 240 is configured to provide excitation light so as to cause light to be emitted by the optodes 211-215. As illustrated, light source 240 may direct excitation light towards the optode 213. In this example scenario, analyte C (246) is present within a detectable concentration level and/or a detectable distance from the optode 213.

In response to receiving the excitation light from the light source 240, optode 213 may emit emission light 244. Furthermore, in response to analyte C (246) being nearby with a sufficient concentration, at least a portion of the emission light 244 may be quenched, enhanced, or otherwise modified. The emission light 244 may be filtered by optical filter 223 as filtered light 248. Among other properties, filtered light 248 may include a relatively small portion of light at the excitation wavelength(s). In other words, the optical filter 223 may be selected and/or configured to filter at least a substantial portion of the excitation wavelengths from the emission light 244.

The filtered light 248 may be sensed by detector element 233. The detector element 233 may provide information indicative of sensing analyte C (246) to a controller, such as controller 112 as described in reference to FIG. 1.

Figure 3:
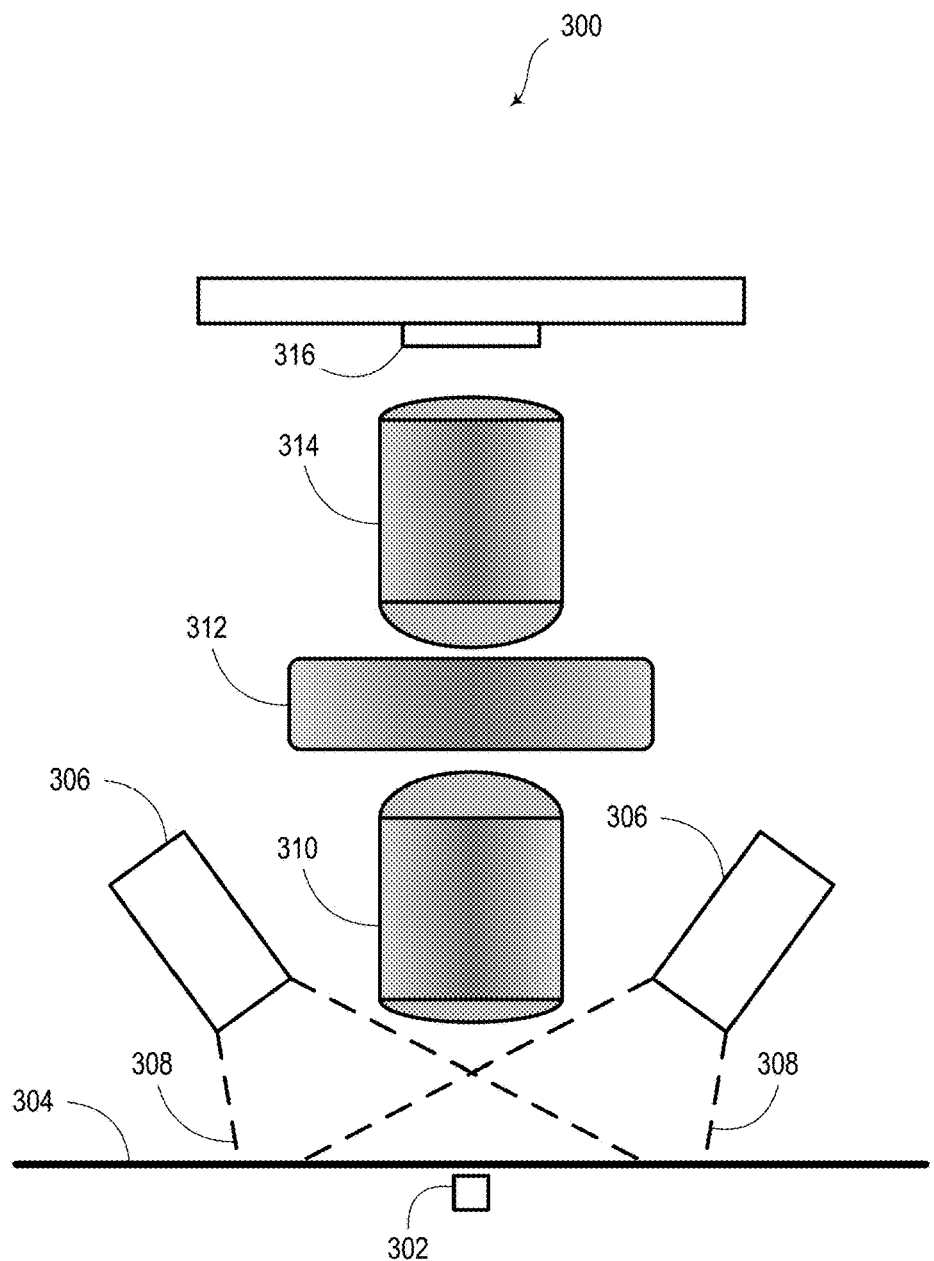
FIG. 3 illustrates a system, according to an example embodiment.

FIG. 3 illustrates a system 300, according to an example embodiment. The elements of system 300 may be similar or identical to corresponding elements from scenario 200 and system 100 as illustrated and described in reference to FIGS. 1 and 2A-2D. In an example embodiment, system 300 may represent a portion of a wearable device having a lensed optical design.

An optode 302 may be injected or otherwise delivered to a location under a skin surface 304. The optode 302 may be configured to emit emission light in response to excitation light having an excitation wavelength. System 300 may be aligned, registered, positioned, or otherwise disposed proximate to a skin surface 304 and the optode 302.

System 300 may include at least one light source 306. The at least one light source 306 may be configured to provide excitation light in an illumination beam 308. The at least one light source 306 may include a laser diode configured to emit light with wavelengths between 630-640 nm at around 140 mW power. In some embodiments, one or more collimation lenses may be disposed proximate to the laser diode(s) so as to collimate the excitation light. For example, the collimation lenses may include a molded acrylic lens.

The system 300 may further include lenses 310 and 314. In an example embodiment, lenses 310 and 314 may be configured to form an achromatic doublet lens set. For example, the achromatic doublet lenses may include a numerical aperture of 0.5 with f1.0 optics. The system 300 may also include an optical filter 312. The optical filter 312 may be a bandpass filter configured to transmit light with wavelengths between 660-700 nm. Accordingly, the optical filter 312 may filter out the excitation light from the laser diode light source(s) 306.

The doublet lenses 310 and 314 may collect light from near the skin surface 304 and focus it onto a detector array 316. In an example embodiment, the detector array 316 may include a CMOS sensor with over 4 million pixels. The detector array 316 may be sensitive to light transmitted through the doublet lenses and the bandpass filter.

The excitation light in the illumination beam 308 may be transmitted, at least in part, to the optode 302. The optode 302 may emit emission light, which may be collected via lens 310. The emission light may be filtered by optical filter 312. Specifically, light with wavelengths outside the optical filter pass band (e.g. excitation light) will be substantially rejected/filtered. The lens 314 may focus the emission light onto the detector array 316.

Figure 4:
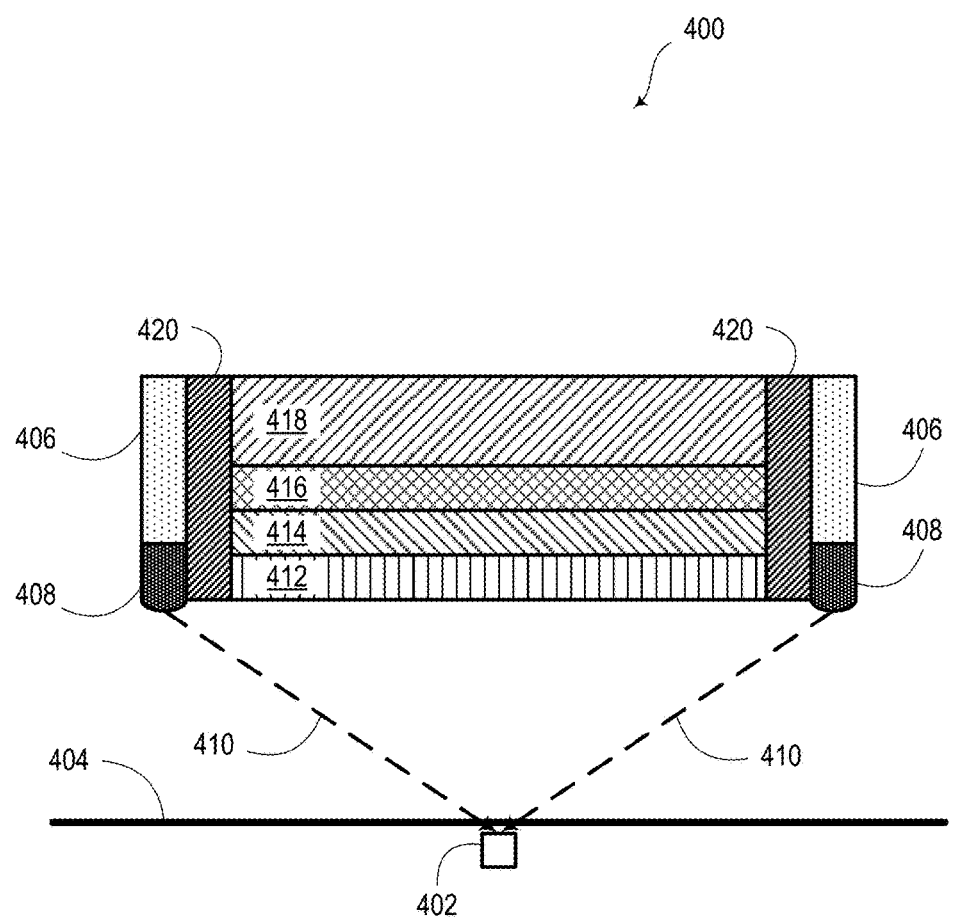
FIG. 4 illustrates a cross-sectional view of a system, according to an example embodiment.

FIG. 4 illustrates a cross-sectional view of a system 400, according to an example embodiment. The elements of system 400 may be similar or identical to corresponding elements illustrated and described in reference to FIGS. 1, 2A-2D, and 3. In an example embodiment, system 400 may represent a portion of a wearable device having a "lensless" optical design. As described herein, lensless optical designs may not include an imaging objective lens. Alternatively or additionally, lensless optical designs may include a lenslet array. The lenslet array may include a plurality of lenslet elements that correspond with, and are aligned to, a plurality of detector elements and/or pixels of an image sensor. In some embodiments, the lenslet array may improve light collection efficiency. It is understood that a variety of other types of lensless optical designs are possible, all of which are contemplated herein.

System 400 may be operable to detect emission light emitted from an optode 402, which may be embedded beneath a skin surface 404. The optode 402 may be configured to emit emission light in response to receiving excitation light.

System 400 includes a light source 406. Light source 406 may include one or more laser diodes. The light source 406 may be optically coupled to a diffuser 408. The diffuser may include a polymeric material, such as acrylic (polymethylmethacrylate). However, other materials configured to diffuse light are contemplated herein.

The system 400 may also include one or more of: a polarization filter 412, an interference filter 414, and an absorptive filter 416. The combination of the polarization filter 412, interference filter 414, and the absorptive filter 416 may be termed the optical filter stack. Alternatively, any subset of the filters may make up the optical filter stack, e.g. a single absorptive filter 416 or a combination of an absorptive filter and an interference filter, etc. The physical order of the respective filters in the optical filter stack is interchangeable. That is, the polarization filter 412, interference filter 414, and the absorptive filter 416 may be arranged in different order within the optical filter stack. The optical filter stack may be configured to transmit at least a portion of the emission light from optode 402 while rejecting substantially all of the excitation light from light source 406. The system 400 may also include an image sensor 418. As described elsewhere herein, the image sensor 418 may include a CMOS or CCD image sensor.

In an example embodiment, one or more of the filters in the optical filter stack may be configured to have different optical transfer functions along a lateral dimension of the one or more filters. For example, the one or more filters of the optical filter stack may be patterned (e.g. via lithographic techniques) so as to have different optical transfer functions based on a location along a lateral dimension of the filter. The different optical transfer functions may include one or more of: a different wavelength/waveband, a different polarization, a different relative optical density, etc. Accordingly, different pixels of the image sensor 418 may receive light having been filtered according to the different optical transfer functions of the optical filter stack based on the respective location of the pixels along the lateral dimension of the image sensor 418.

The system 400 includes a baffle 420, which may be configured to block light from the light source 406 and diffuser 408 from directly entering the optical filter stack.

In an example embodiment, excitation light emitted by the light source 406 may be optically coupled to the diffuser 408, which may diffuse the excitation light so as to spread it across the skin surface 404. Furthermore, the excitation light may impinge on optode 402. In response, the optode 402 may emit emission light. At least a portion of the emission light may be incident on the optical filter stack. Furthermore, at least some of the emission light may be transmitted through the polarization filter 412, the interference filter 414, and the absorptive filter 416 so as to be sensed by the image sensor 418.

It is understood that a variety of other optical configurations are possible to provide excitation light to optodes embedded in tissue and detection of the emission light from the optodes. For example, an edge-emitting laser diode may be coupled into a light guide film. The light guide film may be configured to guide excitation light from the edge-emitting laser diode along a plane parallel to the image sensor. At least a portion of the excitation light may be reflected and/or refracted out of the plane and toward the skin surface (and the embedded optode(s)).

In another embodiment, a light source may transilluminate optodes from an "opposite side" of the skin surface. That is, the light source may be located on an opposing skin surface from the image sensor and optical filter(s). For example, the light source may transilluminate an optode embedded in an earlobe through a backside of the earlobe.

In yet another embodiment, the light source may be coupled to a dichroic prism. In such a scenario, the light source may emit excitation light that may be refracted towards the skin surface via a dichroic beam splitter or prism. That is, at least based on the wavelength of the excitation light, the excitation light may be diverted out of plane towards the skin surface and the embedded optode(s). The dichroic beam splitter/prism may be configured to transmit emission light from the optodes substantially through the beam splitter and towards the optical filter stack and image sensor.

In a further embodiment, a laser diode may illuminate a spatial light modulator with excitation light. The spatial light modulator may controllably direct the excitation light towards a dichroic beam splitter/prism. The dichroic beam splitter/prism may be configured to refract light at the excitation wavelength(s) out of plane towards the optodes embedded under the skin surface. In other words, a combination of a spatial light modulator and a dichroic beam splitter may enable spatially-controllable illumination of discrete optodes embedded in the skin surface.

In addition to a spatial light modulator, systems described herein may generally provide modulated light via other devices and systems in an effort to improve signal to noise ratio in the presence of physiometric noise, e.g. autofluorescence. For example, a laser diode may illuminate the tissue at a given pulse frequency. In such a scenario, various lock-in and/or heterodyne signal amplification/isolation techniques may be used in an effort to improve the signal to noise ratio of the desired signal (e.g. light output from the plurality of optodes) by substantially rejecting all other signals that are not at the pulse frequency.

Figure 5A:
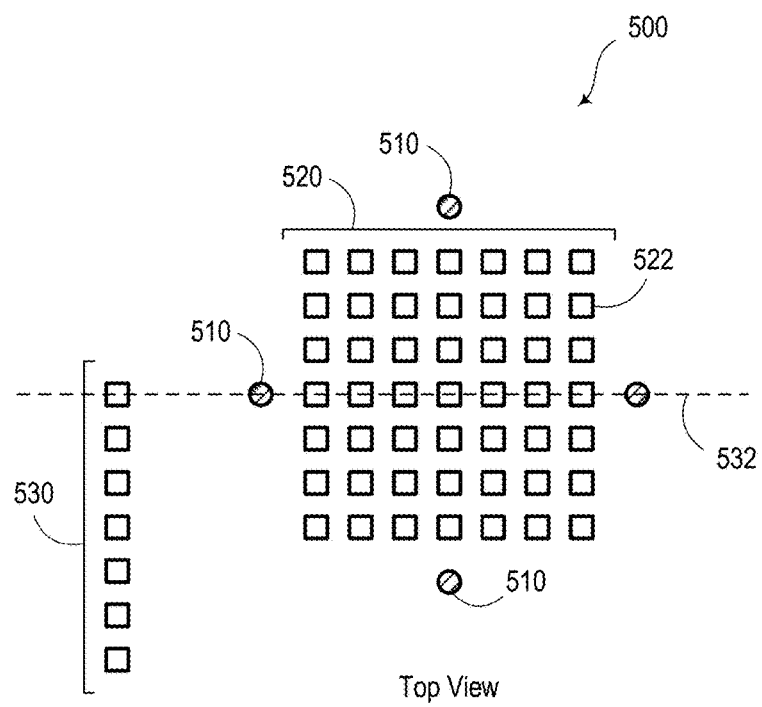
FIG. 5A illustrates a top view of a system, according to an example embodiment.

FIGS. 5A-5D illustrate various views of systems, according to several example embodiments. FIG. 5A illustrates a top view of a system 500. Elements of system 500 may be similar or identical to elements illustrated and described in reference to FIGS. 1, 2A-2D, 3, and 4. System 500 may include a plurality of light sources 510, a primary detector array 520, and a calibration detector array 530. As described elsewhere herein, light sources 510 may include laser diodes configured to emit excitation light. As illustrated, the light sources 510 may be arranged around a perimeter of the primary detector array 520. However, other arrangements are possible.

The primary detector array 520 and the calibration detector array 530 may include a plurality of detector elements 522. As described herein, the detector element 522 may include one or more pixels of a CMOS image sensor.

In an example embodiment, the detector elements 522 of the primary detector array 520 may be arranged in a square array. In such a scenario, a center-to-center distance between respective detector elements 522 of the primary detector array 520 may be 0.7 millimeters. Other distances are contemplated.

In an example embodiment, the secondary detector array 530 may include a linear arrangement of detector elements 522. The secondary detector array 530 may be operable to calibrate autofluorescence properties of tissue. That is, autofluorescence may vary substantially between individuals as well as between tissue locations. As such, a local calibration array may enable optical measurements with better rejection of autofluorescence signals.

Figure 5B:
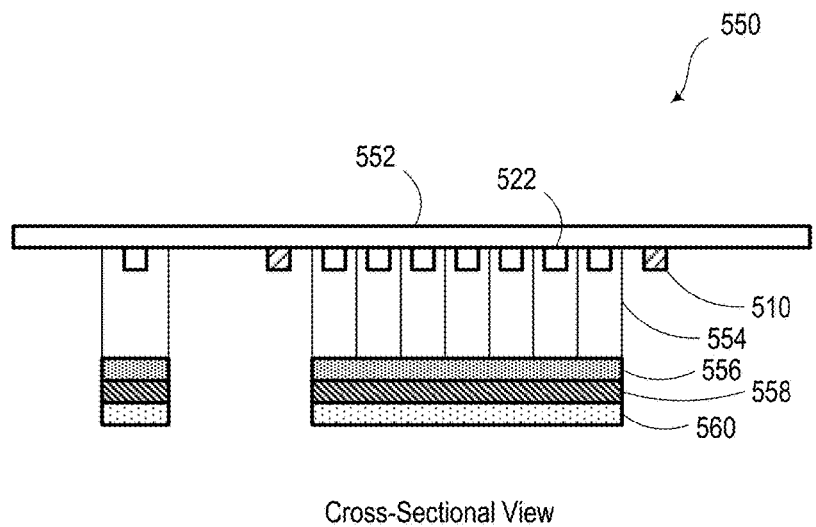
FIG. 5B illustrates a cross-sectional view of a system, according to an example embodiment.

FIG. 5B illustrates a cross-sectional view of a system 550, according to an example embodiment. The cross-sectional view of system 550 may be provided along reference line 532 of FIG. 5A. The system 550 may include a substrate 552. In an example embodiment, the substrate 552 may include a printed circuit board, however other substrate materials are possible.

The system 550 may include baffles 554 that may provide an opaque barrier between individual detector elements 522. The baffles 554 may also be operable to prevent stray excitation light produced by light sources 510 from directly impinging upon the detector elements 522. The system 550 may also include an optical filter 556, a lenslet array 558, and a aperture plate 560. The lenslet array 558 may provide optical power for discrete detector elements 522 and their corresponding portions of the optical filter 556. The system 550 may also include an aperture plate 560. The aperture plate 560 may be configured to provide coarse spatial dependence. That is, by providing an aperture for each relatively large detector element/channel, spatial information about a rough location of one or more optodes may be obtained.

In some embodiments, aperture plate 560 may include a plurality of slits. Additionally or alternatively, aperture plate 560 may include a plurality of aperture holes that correspond to locations of the detector elements 522.

Figure 5C:
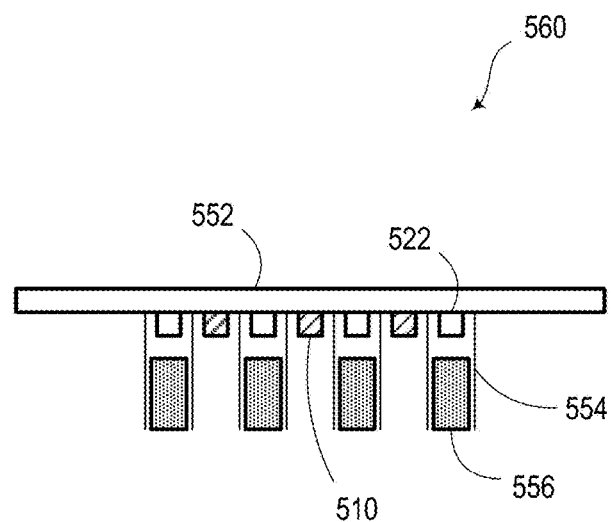
FIG. 5C illustrates a cross-sectional view of a system, according to an example embodiment.

FIG. 5C illustrates a cross-sectional view of a system 560, according to an example embodiment. The elements of system 560 may be similar or identical to system 550; however an arrangement of various elements may differ. For example, light sources 510 may be interleaved between detector elements 522 of the detector array. Furthermore, an optical channel for each detector element 522 may be baffled from other detector elements and the light sources 510 by a plurality of baffles 554. The baffles 554 may be substantially opaque to excitation light. In an example embodiment, the baffles 554 include a metalized channel. Additionally or alternatively, an optical filter 556 (e.g. an absorbtive filter) may be present in each optical channel.

System 560 may provide higher intensity excitation light for the optodes and may enable simultaneous measurement of the autofluorescence background and an emission light signal.

Figure 5D:
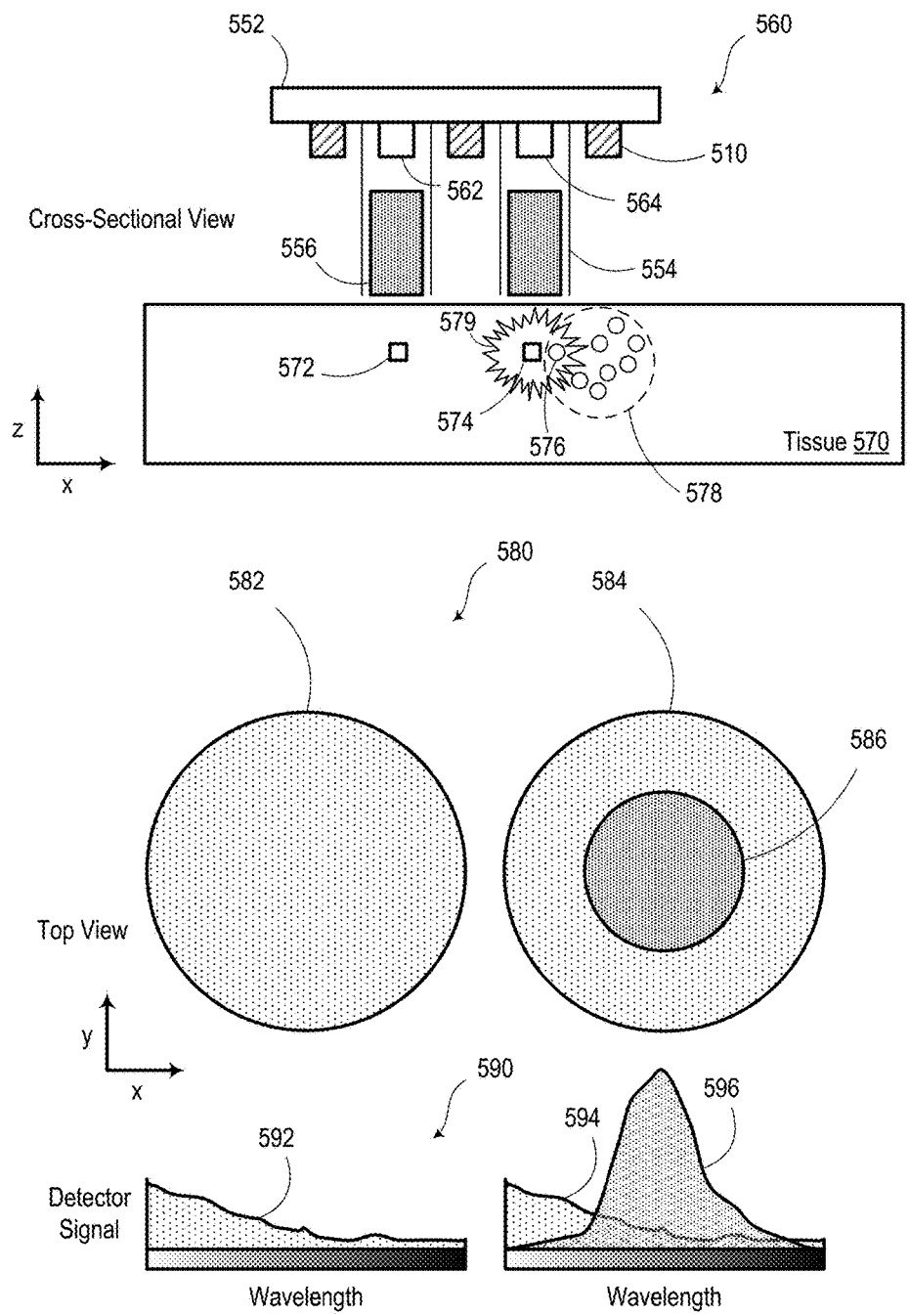
FIG. 5D illustrates a cross-sectional view of a system and representative detector signals, according to an example embodiment.

FIG. 5D illustrates a cross-sectional view of a system 560, a top-view of light emissions 580 and representative detector signals 590, according to an example embodiment. For purposes of illustration, system 560 may include two detector elements 562 and 564. The detector elements 562 and 564 may have respective baffles 554 and respective optical filters 556. The detector elements 562 and 564 may be arranged on a substrate 552 such that a plurality of light sources 510 may be arranged around and/or between the detector elements 562 and 564.

In an example embodiment, system 560 may be in proximity to tissue 570. For example, the system 560 may be a part of a mobile device, which may be moved into contact with a skin surface. Alternatively, contact with the skin surface need not be necessary. In such scenarios, optodes 572 and 574 may have previously been implanted in the tissue 570. In some cases, a lateral spacing (e.g. along the x-direction) between the optodes 572 and 574 may correspond to a lateral spacing between the detector elements 562 and 564.

As illustrated in FIG. 5D, the tissue 570 may include a suspect skin area 578. In such a scenario, the suspect skin area 578 may include a suspicious skin spot, tissue mass, etc. As such, in some cases, the suspect skin area 578 may include a plurality of analytes (e.g. cancer cells or other types of cells indicative of a particular medical condition). The plurality of analytes may include analyte 576. Optode 574 may provide a characteristic optical response 579 in response to being in proximity to the analyte 576. In an example embodiment, the characteristic optical response 579 may include a characteristic optical response with wavelengths in the near-infrared. Other optical responses and wavelengths are possible.

In the scenario described above, FIG. 5D may illustrate a top view of light emissions 580 from the optodes 572 and 574 and/or the region around the optodes 572 and 574. For example, light sources 510 may illuminate the tissue 570 near the optodes 572 and 574. In response to the excitation light, the tissue 570 may autofluoresce. That is, the tissue 570 near the optodes 572 and 574 may naturally emit light in response to absorbing the excitation light from light sources 510.

In some cases, optodes 572 and 574 may be configured to fluoresce when illuminated with excitation light and while in proximity to the analyte 576. In such a scenario, the optode 574 may provide characteristic optical response 586. Thus, detector 562 may receive light from an autofluorescence response 582 while detector 564 may receive light from an autofluorescence response 584 and characteristic optical response 586.

Accordingly, the spectral waveforms of light received by detectors 562 and 564 may vary. For example, in the above example, detector 562 may provide detector signal 592, which may correspond to the autofluorescence response 582. Furthermore, detector 564 may provide a superposition of detector signal 594 and detector signal 596. That is, a signal from detector 564 may include an autofluorescence response 584 and a characteristic optical response 586.

In such scenarios, various noise-reduction techniques may be applied to improve signal-to-noise ratio. For example, detector signal 592 may be integrated versus wavelength to provide a baseline autofluorescence correction factor. As such, the autofluorescence correction factor may be subtracted from integrated detector signals 594 and 596.

Other noise-reduction techniques based on wavelength and/or spatial locations are possible. As an example, noise-reduction techniques may be based on tissue optical properties and/or optode depth within the tissue.

It is understood that other optical arrangements are possible so as to determine spatial information about a presence or absence of an analyte in skin tissue using optodes. Such other optical arrangements are contemplated herein.

III. Example Methods

Figure 6:
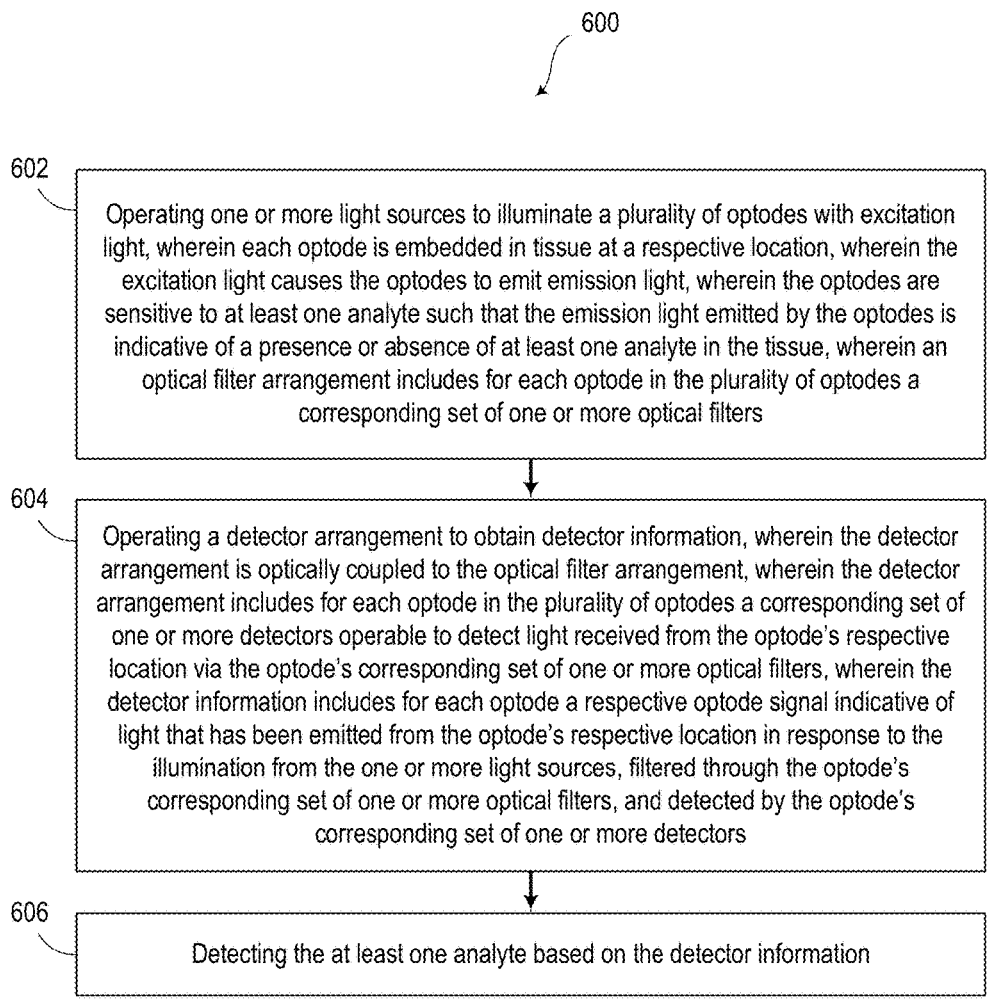
FIG. 6 illustrates a method, according to an example embodiment.

FIG. 6 illustrates a method 600, according to an example embodiment. The method 600 may include various blocks or steps. The blocks or steps may be carried out individually or in combination. The blocks or steps may be carried out in any order and/or in series or in parallel. Further, blocks or steps may be omitted or added to method 600.

The blocks of method 600 may be carried out by various elements of the systems 100, 300, 400, 500, 550, and 560 as illustrated and described in reference to FIGS. 1, 3, 4, 5A, 5B, 5C, and 5D.

Block 602 includes operating one or more light sources (e.g. light source 102) to illuminate a plurality of optodes (e.g. optode array 122) with excitation light. The one or more light sources may include a light-emitting diode and/or a laser diode. As described elsewhere herein, each optode may be embedded in tissue at a respective location. The excitation light may cause the optodes to emit emission light. For example, the optodes may include a chemical, such as a fluorophore, which may be configured to fluoresce in response to receiving the excitation light. Furthermore, the optodes are configured to change their optical properties in response to a presence or an absence of at least one analyte. That is, the optodes may exhibit optical sensitivity to the at least one analyte such that the emission light emitted by the optodes is indicative of a presence or absence of the at least one analyte in the tissue.

An optical filter arrangement (e.g. optical filter arrangement 106) includes for each optode in the plurality of optodes a corresponding set of one or more optical filters. The optical filters may include at least one of: a bandpass filter, a longpass filter, a shortpass filter, a dichroic filter, a polarization filter, an interference filter, or an absorptive filter. Other types of optical filters or optical elements are possible.

Block 604 includes operating a detector arrangement (e.g. detector arrangement 110) to obtain detector information. The detector arrangement is optically coupled to the optical filter arrangement. In some embodiments, the one or more light sources are disposed in an interleaved arrangement with respect to the detectors in the detector arrangement.

Furthermore, the detector arrangement includes for each optode in the plurality of optodes a corresponding set of one or more detectors operable to detect light received from the optode's respective location via the optode's corresponding set of one or more optical filters. The detector information includes for each optode a respective optode signal indicative of light that has been emitted from the optode's respective location in response to the illumination from the one or more light sources, filtered through the optode's corresponding set of one or more optical filters, and detected by the optode's corresponding set of one or more detectors.

Block 606 includes detecting the at least one analyte based on the detector information. In such a scenario, a presence or absence of the at least one analyte may be determined via the described method 600.

The method 600 may optionally include determining a background signal based on the detector information. In such a scenario, the background signal may include a tissue autofluorescence signal. For example, a background signal may be obtained by illuminating skin tissue that does not have embedded optodes. The emitted light from such tissue may be indicative of a background autofluorescence signal. Additionally, the method 600 may include adjusting the detector information based on the background signal. That is, the background signal may be subtracted from the detector information in a wavelength- or spatially-dependent manner. For example, background subtraction and/or other noise reduction methods may be possible based on optical properties of tissue and optode depth within the tissue.

The method 600 may optionally include adjusting each of the optode signals based on a corresponding portion of the background signal. That is, the background signal may be subtracted from each optode signal in a wavelength dependent manner so as to reduce the influence of tissue autofluorescence on the analyte detection technique.

Figure 7:
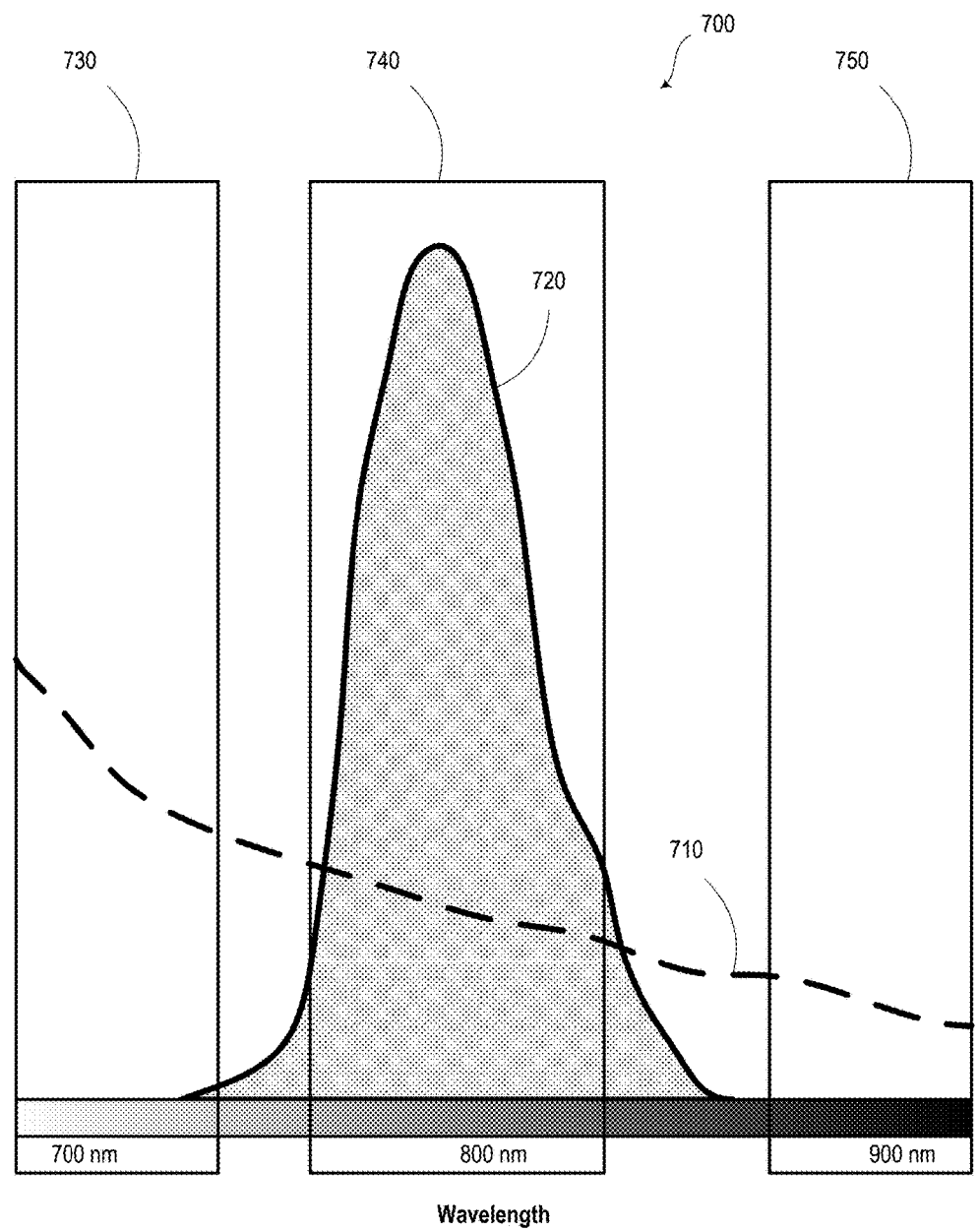
FIG. 7 illustrates several waveforms, according to an example embodiment.

FIG. 7 illustrates several waveforms 700, according to an example embodiment. The several waveforms 700 may include an autofluorescence waveform 710 and an emission waveform 720. Furthermore, FIG. 7 includes several wavebands corresponding to several bandpass filters. For example, waveband 730 may correspond to a bandpass filter with a pass band substantially between 700 nm and 730 nm. Waveband 740 may correspond to a bandpass filter with a pass band substantially between 760 nm to 820 nm. Furthermore, waveband 750 may correspond to a bandpass filter with a pass band substantially between 875 nm and 900 nm. It is understood that such wavebands are provided for illustration only and other wavelengths and wavebands are possible.

In some example embodiments, an optode signal may include an emission portion (e.g. emission waveform 720) and a corresponding autofluorescence portion (e.g. autofluorescence waveform 710). In such a scenario, the emission portion may be indicative of light from the optode's location that is filtered by a first optical filter (e.g. a filter with waveband 740) in the optode's corresponding set of optical filters. Likewise, the autofluorescence portion is indicative of light from tissue at the optode's location that is filtered by a second optical filter (e.g. a filter with waveband 730 or 750) in the optode's corresponding set of optical filters. Thus, adjusting each of the optode signals based on a corresponding portion of the background signal may include adjusting the emission portions of the optode signals with respect to the corresponding autofluorescence portions.

In some embodiments, the emission light may represent a characteristic signal over a characteristic waveband. That is, emission waveform 720 may include certain identifying characteristics. For example, emission waveform 720 includes a characteristic signal shape having a peak wavelength around 800 nm and a characteristic waveband of approximately 760 nm to 820 nm. Other identifying characteristics are possible.

Such identifying characteristics may be utilized in cancelling or reducing the autofluorescence background signal. For example, an integrated signal from the three filter windows 730, 740, and 750 may be used to correct the autofluorescence background if functional forms (e.g. the autofluorescence and emission waveforms) are known, or may be at least approximated or predicted.

In such a scenario, several detector "channels" may be used, each with a different filter window in an effort to obtain optical information from a plurality of spectral windows. As such, a substantial portion of the background autofluorescence may be cancelled.

Other methods and systems are contemplated to reduce or eliminate background signals. For example, a spectral unmixing method may be used in conjunction with machine learning to find an optimal reduction in background noise for a given set of filters, spectral windows, and approximate emission and autofluorescence waveforms.

Furthermore, methods and systems that utilize lock-in amplification, phase-locked loops, homodyne detection, heterodyne detection, and/or other methods for reducing background signal noise are contemplated herein.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:

1. A system, comprising:
   a plurality of optodes configured to be embedded in tissue, wherein each optode is at a respective location, wherein an excitation light causes the optodes to emit emission light, and wherein the optodes are sensitive to at least one analyte such that the emission light emitted by the optodes is indicative of a presence or absence of at least one analyte in the tissue;
   one or more light sources, wherein the one or more light sources are configured to illuminate the plurality of optodes with the excitation light;
   an optical filter array, wherein the optical filter array includes for each optode in the plurality of optodes a corresponding plurality of optical filters;
   a detector array optically coupled to the optical filter array, wherein the detector array includes for each optode in the plurality of optodes a corresponding plurality of detectors configured to detect light received from the optode's respective location via the optode's corresponding plurality of optical filters; and
   a controller comprising at least one processor, wherein the controller is programmed to carry out operations, the operations comprising:
      operating the one or more light sources to illuminate the plurality of optodes with excitation light;
      operating the detector array to obtain detector information, wherein the detector information includes for each optode a respective optode signal indicative of light that has been emitted from the optode's respective location in response to the illumination from the one or more light sources, filtered through the optode's corresponding plurality of optical filters, and detected by the optode's corresponding plurality of detectors; and detecting at least one analyte based on the detector information.

2. The system of claim 1, wherein the one or more light sources:

are disposed in an interleaved arrangement with respect to the detectors in the detector array, and comprise at least one of: a light-emitting diode or a laser diode.

3. The system of claim 1, further comprising a diffuser, wherein the one or more light sources are optically-coupled to the diffuser, and wherein the diffuser is disposed around the detector array.

4. The system of claim 1, further comprising a spatial light modulator, wherein the operations further comprise selecting a target optode from the plurality of optodes and controlling the spatial light modulator to direct the excitation light from at least one of the one or more light sources toward the target optode in the plurality of optodes.

5. The system of claim 1, wherein the operations further comprise:

determining a background signal based on the detector information, wherein the background signal comprises a tissue autofluorescence signal; and adjusting the detector information based on the background signal.

6. The system of claim 5, wherein adjusting the detector information based on the background signal comprises adjusting each of the optode signals based on a corresponding portion of the background signal.

7. The system of claim 6, wherein each optode's respective optode signal includes an emission portion and a corresponding autofluorescence portion, wherein the emission portion is indicative of light from the optode's location that is filtered by a first optical filter in the optode's corresponding set of optical filters, wherein the autofluorescence portion is indicative of light from the optode's location that is filtered by a second optical filter in the optode's corresponding set of optical filters, and wherein adjusting each of the optode signals based on a corresponding portion of the background signal comprises adjusting the emission portions of the optode signals based on the corresponding autofluorescence portions.

8. The system of claim 1, wherein the one or more optical filters comprise at least one of: a bandpass filter, a longpass filter, a shortpass filter, a dichroic filter, a polarization filter, an interference filter, or an absorptive filter.

9. The system of claim 8, wherein the characteristic waveband comprises a characteristic long wavelength cutoff and a characteristic short wavelength cutoff, wherein the plurality of optical filters further comprise a shortpass filter, wherein the shortpass filter has a cutoff wavelength less than the characteristic short wavelength cutoff.

10. The system of claim 8, wherein the characteristic waveband comprises a characteristic long wavelength cutoff and a characteristic short wavelength cutoff, wherein the one or more optical filters further comprise a longpass filter, wherein the longpass filter has a cutoff wavelength greater than the characteristic long wavelength cutoff.

11. The system of claim 1, wherein the emission light comprises a characteristic signal over a characteristic waveband, wherein the one or more optical filters comprise a bandpass filter, wherein the bandpass filter is configured to substantially transmit light over the characteristic waveband.

12. The system of claim 1, wherein the one or more light sources and the plurality of detectors are arranged in a checkerboard pattern corresponding with the respective locations of the plurality of optodes.

13. A method comprising:

operating a plurality of optodes embedded in tissue, wherein each optode is at a respective location, wherein an excitation light causes the optodes to emit emission light, wherein the optodes are sensitive to at least one analyte such that the emission light emitted by the optodes is indicative of a presence or absence of at least one analyte in the tissue;

operating one or more light sources to illuminate the plurality of optodes with the excitation light, wherein an optical filter array includes for each optode in the plurality of optodes a corresponding plurality of optical filters;

operating a detector array to obtain detector information, wherein the detector array is optically coupled to the optical filter array, wherein the detector array includes for each optode in the plurality of optodes a corresponding plurality of detectors operable to detect light received from the optode's respective location via the optode's corresponding plurality of optical filters, wherein the detector information includes for each optode a respective optode signal indicative of light that has been emitted from the optode's respective location in response to the illumination from the one or more light sources, filtered through the optode's corresponding plurality of optical filters, and detected by the optode's corresponding plurality of detectors; and detecting at least one analyte based on the detector information.

14. The method of claim 13, wherein the one or more light sources:

are disposed in an interleaved arrangement with respect to the detectors in the detector array, and comprise at least one of: a light-emitting diode or a laser diode.

15. The method of claim 13, further comprising:

determining a background signal based on the detector information, wherein the background signal comprises a tissue autofluorescence signal; and adjusting the detector information based on the background signal.

16. The method of claim 15, wherein adjusting the detector information based on the background signal comprises adjusting each of the optode signals based on a corresponding portion of the background signal.

17. The method of claim 16, wherein each optode's respective optode signal includes an emission portion and a corresponding autofluorescence portion, wherein the emission portion is indicative of light from the optode's location that is filtered by a first optical filter in the optode's corresponding set of optical filters, wherein the autofluorescence portion is indicative of light from the optode's location that is filtered by a second optical filter in the optode's corresponding set of optical filters, and wherein adjusting each of the optode signals based on a corresponding portion of the background signal comprises adjusting the emission portions of the optode signals based on the corresponding autofluorescence portions.

18. The method of claim 13, wherein the one or more optical filters comprise at least one of: a bandpass filter, a longpass filter, a shortpass filter, a dichroic filter, a polarization filter, an interference filter, or an absorptive filter.

19. The method of claim 13, wherein the emission light comprises a characteristic signal over a characteristic waveband, wherein the one or more optical filters comprise a bandpass filter, wherein the bandpass filter is configured to substantially transmit light over the characteristic waveband.

20. The method of claim 13, further comprising:
   determining a background signal based on at least one of:
      detecting light via one or more detectors located at respective locations within the detector array or detecting light not having a characteristic optical response, wherein the characteristic optical response comprises the emission light emitted by the optodes that is indicative of the presence or absence of at least one analyte in the tissue, wherein the background signal comprises a tissue autofluorescence signal; and
   adjusting the detector information based on the background signal.

21. The method of claim 13, wherein the one or more light sources and the plurality of detectors are arranged in a checkerboard pattern corresponding with the respective location of the plurality of optodes.

* * * * *